(12) United States Patent
Lu et al.

(10) Patent No.: US 6,881,955 B2
(45) Date of Patent: Apr. 19, 2005

(54) METROLOGY PROCESS FOR ENHANCING IMAGE CONTRAST

(75) Inventors: Wei Lu, Poughkeepsie, NY (US); John Charles Petrus, Standfordville, NY (US)

(73) Assignee: International Business Machines Corporation, Armonk, NY (US)

( * ) Notice: Subject to any disclaimer, the term of this patent is extended or adjusted under 35 U.S.C. 154(b) by 48 days.

(21) Appl. No.: 10/604,110

(22) Filed: Jun. 26, 2003

(65) Prior Publication Data

US 2004/0262518 A1 Dec. 30, 2004

(51) Int. Cl.[7] .............................................. G01N 23/225
(52) U.S. Cl. ...................................... 250/307; 250/310
(58) Field of Search ................................. 250/307, 310, 250/309

(56) References Cited

U.S. PATENT DOCUMENTS

| | | |
|---|---|---|
| 4,226,666 A | 10/1980 | Winters et al. |
| 5,009,743 A | 4/1991 | Swann |
| 5,188,705 A | 2/1993 | Swanson et al. |
| 5,376,791 A | 12/1994 | Swanson et al. |
| 6,303,932 B1 | 10/2001 | Hamamura et al. |
| 6,509,197 B1 | 1/2003 | Satya et al. |
| 6,677,586 B1 * | 1/2004 | Nasser-Ghodsi et al. ... 250/310 |
| 2002/0019137 A1 | 2/2002 | Tsung et al. |
| 2002/0195422 A1 | 12/2002 | Sievers et al. |

* cited by examiner

*Primary Examiner*—Jack I. Berman
(74) *Attorney, Agent, or Firm*—Lisa U. Jaklitsch; Cantor Colburn LLP

(57) ABSTRACT

A metrology process for increasing image contrast of a buried feature, comprising milling a selected surface of a substrate to expose a cross section of the buried feature; exposing the exposed cross section with a gas mixture, wherein the gas mixture comprises a flourine bearing compound; and irradiating the exposed cross section with a high energy beam to increase image contrast of the buried feature.

20 Claims, 3 Drawing Sheets

METROLOGY PROCESS FOR ENHANCING IMAGE CONTRAST

BACKGROUND OF INVENTION

The present disclosure generally relates to metrology, and more particularly, to a metrology process for enhancing image contrast and discrimination.

In the semiconductor integrated circuit (IC) industry, there is a continuing demand for higher circuit packing densities. This demand of increased packing densities has led the semiconductor industry to develop new materials and processes to achieve sub-micron device dimensions. Manufacturing IC's at such minute dimensions adds more complexity to circuits and the demand for improved methods to inspect integrated circuits in various stages of their manufacture is ever present.

Although inspection of such products at various stages of manufacture is very important and can significantly improve production yield as well as product reliability, the increased complexity of IC's increases the cost of such inspections, both in terms of expense and time. However, if a defect can be detected early in production, the cause of the defect can be determined and corrected before a significant number of defective IC's are manufactured.

A problem with current inspection techniques is the lack of image contrast for the various layers employed in the device manufacture. problem is exacerbated as a result of higher circuit packing densities. Especially lacking is the image contrast between oxide and nitride layers in, for example, a polygate structure.

Dual beam tools combine focused ion beam, scanning electron microscopy, as well as other capabilities in a single tool. Focused ion beam (FIB) technology focuses an ion beam from an ion source through a lens and irradiates the beam onto a sample. In the fabrication of integrated circuits, FIB is frequently used to mill away (etch) material by irradiating an ion beam of relatively high current onto the substrate. The focused ion beam can be directed to a very small point on the semiconductor device and then scanned, raster fashion, over a surface where the desired material is to be removed. As an ion impinges on the semiconductor device surface, its momentum is transferred, resulting in the removal of one or more surface atoms according to a process called sputtering. By selecting a raster pattern of a given overall shape, for example a horizontal raster pattern, a correspondingly shaped area of surface material can be removed. Often several successive layers of a semiconductor device are removed in a given area in order to reach an underlying layer. However, the reaction products produced by milling have a tendency to redeposit onto the surfaces of the substrate causing contrast problems during imaging of cross sections provided by the milling process.

Injecting gases that preferentially mill particular materials, such as dielectric or conductive materials, can enhance the rate and controllability of milling. Gases are locally injected near the surface of the semiconductor device during the milling process to increase the efficiency of removing a specific type of material. As the boundaries between different materials are traversed, the type of gas injected may be changed to conform to the requirements of the new material; that is, a different gas may be used for each material or class of materials. Such techniques can be used to selectively expose the integrated circuit structure for probing or examination, cut holes through power and ground planes, and to selectively sever conductors. For example, U.S. Pat. Nos. 5,188,705 and 5,376,791 to Swanson et al. disclose the use of a focused ion beam for sputtering (etching) of semiconductor devices while directing iodine vapor toward the surface to enhance the removal of materials such as silicon and aluminum. See also U.S. Pat. No. 5,009,743 to Swann, which describes the use of dual ion guns in combination with injection of molecular iodine, and U.S. Pat. No. 4,226,666 to Winters et al., which describes etching employing electron-beam or ion-beam radiation and a noble gas halide such as $XeF_2$, $XeF_4$, $XeF_6$, $KrF_2$, $KrF_4$ and $KrF_6$. The use of $XeF_2$ with FIB for preferential etching of dielectric in semiconductor devices has become commonplace as the use of $XeF_2$ substantially increases the etching rate of dielectric relative to the etching rate of most metals so that conductors can be exposed rapidly and with less risk of electrostatic discharge damage.

New processes and materials required for the higher circuit densities have proven difficult to analyze and control with traditional top down metrology processes. Dual beam tools provide cross-sectioning capability to directly measure and image these complex structures. However, current dual beam processes do not provide adequate image contrast of all the various layers employed in the higher circuit packing densities. For example, current processes fail to provide adequate image contrast between nitride and oxide layers, or different nitride layers.

Accordingly, there remains a need for improved metrology processes for inspection of complicated circuit patterns for defect control.

SUMMARY OF INVENTION

Disclosed herein is a metrology process for increasing image contrast of a buried feature, comprising milling a selected surface of a substrate to expose a cross section of the buried feature; exposing the exposed cross section with a gas mixture, wherein the gas mixture comprises a fluorine bearing compound; and irradiating the exposed cross section with a high energy beam to increase image contrast of the buried feature.

In another embodiment, a metrology process for enhancing an image contrast between an oxide layer in contact with a nitride layer; comprises exposing a cross section comprising the oxide layer in contact with the nitride layer with a gas mixture, wherein the gas mixture comprises a fluorine bearing compound; and irradiating the exposed cross section with an ion beam or an electron beam or a laser or a plasma to increase image contrast between the oxide layer and the nitride layer.

The above described and other features are exemplified by the following figures and detailed description.

BRIEF DESCRIPTION OF DRAWINGS

Referring now to the figures, which are exemplary embodiments and wherein the like elements are numbered alike.

DETAILED DESCRIPTION

Figure 1:
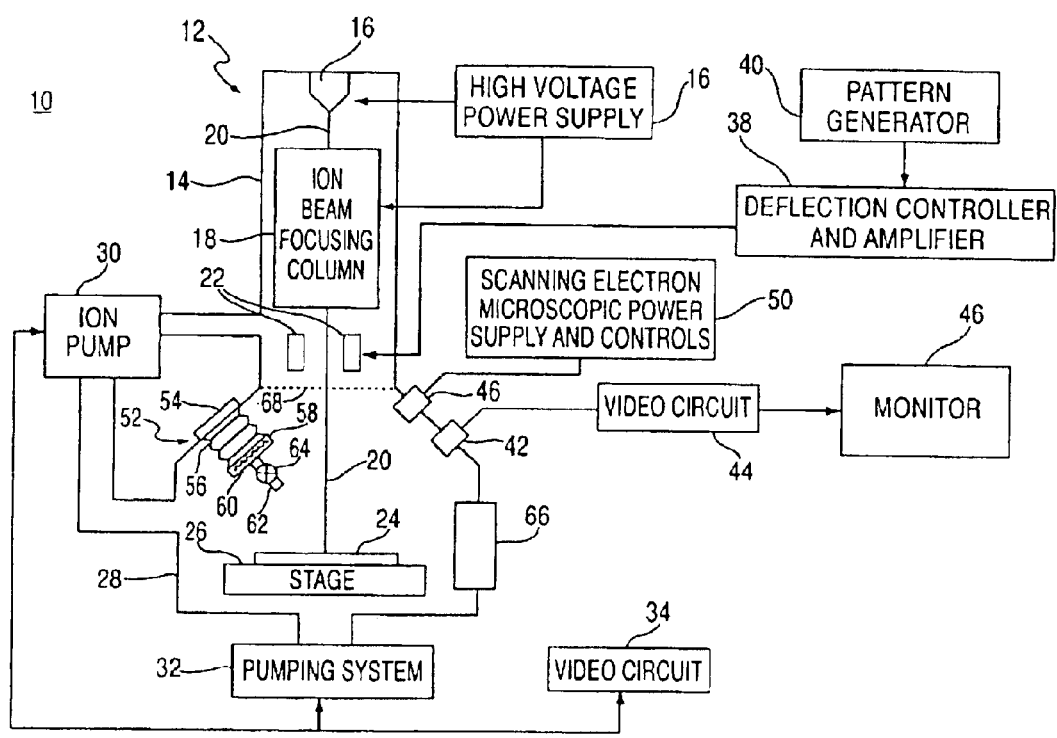
FIG. 1 is schematic diagram of an exemplary focused ion beam system.

A metrology process for increasing image contrast of a buried feature generally includes milling a selected portion of the substrate to expose a cross section of the buried feature and subsequently exposing the cross section to a high energy beam while simultaneously exposing the cross section to a fluorine containing gas. Alternatively, the cross section of the buried feature is exposed to a dilute hydrofluoric acid solution. It has been found that the so-treated cross section results in improved image contrast. While not wanting to be bound by theory, the resulting cross section provides improved topography and image contrast between the various layers forming the cross section. It is believed that the process effectively removes the matter re-deposited during the milling step, thereby providing improved image contrast.

The milling process preferably comprises exposing the selected surface of the substrate to a focused ion beam or a like milling tool. The focused ion beam is preferably oriented perpendicular to the major plane of the substrate to provide a cross section of the buried feature. The cross section of the buried feature is then exposed to a gas mixture and a high energy beam such as the focused ion beam or e-beam or laser or plasma beam to increase the image contrast of the buried feature. A scanning electron micrograph image can then be taken at an angle less than 90 degrees to the cross section, wherein the various layers forming the buried feature can be easily discriminated and effectively analyzed. The milling process may further comprise a gas mixture for enhancing the selectively etching of the substrate as is known in the art. The gas mixture selected for enhancing the milling process preferably comprises a noble gas halide. Suitable noble gas halides include $XeF_2$, $XeF_4$, $XeF_6$, $KrF_2$, $KrF_4$ and $KrF_6$. The focused ion beam reaction products migrate into the vacuum chamber and are subsequently removed by vacuum. However, as previously noted, some of these reaction products may redeposit onto the exposed surface of the cross section and detrimentally affect image contrast of the cross section.

Exposing the cross section to a high-energy beam while simultaneously exposing the cross section to a fluorine containing gas removes the redeposited material and/or provides topography to the various layers forming the cross section. As such, image contrast is markedly improved. Suitable high energy beams are those energy beams sufficient to break the bonds formed in and about the redeposited material including, but not limited to, plasma beams, ion beams, electron beams and laser beams. The gas mixture for providing contrast enhancement preferably comprises a fluorine-containing compound. Preferred fluorine-containing compounds include those compounds that generate fluorine reactive species when exposed to the focused ion beam, e-beam, or the like. Preferably, the fluorine containing compound is a gas at processing conditions and is selected from the group consisting of a compound having the general formula $C_xH_yF_z$, wherein x ranges from 1 to 4, y ranges from 0 to 9 and z ranges from 1 to 10, HF, $NF_3$, $F_2$ and $SF_6$. More preferably, the fluorine-containing compound is $CF_4$ or $NF_3$.

In the alternative embodiment, the fluorine-containing compound is an aqueous hydrofluoric acid (HF) solution. Preferably, the HF solution is at a concentration of less than about 2 percent by volume, with less than about 1 percent more preferred, and with less than about 0.5 percent even more preferred. Also preferred, the HF solution is at a concentration greater than about 0.001 percent by volume, and with greater than about 0.1 percent more preferred. The HF solution is introduced to the substrate and is optionally exposed to the high energy beam to improve the image contrast of the cross section.

The fluorine-containing compounds in the gas mixture are preferably less than about 90 percent by volume of the total volume of the gas mixture to maximize image contrast. More preferably, the fluorine-containing compound is less than about 80 percent by volume of the total gas mixture volume, and with about less than about 70 percent even more preferred. A preferred gas mixture comprises $CF_4$ at about 80 volume percent with the remainder $O_2$ or NO or a mixture thereof.

In a preferred embodiment, the second gas mixture comprises an oxidizing gas in addition to the fluorine-containing compound. Suitable oxidizing gases include, but are not intended to be limited to, $O_2$, NO, water vapor, and the like. A preferred gas mixture comprises $CF_4$ at about 80 volume percent with the remainder $O_2$ or NO or a mixture thereof.

In a preferred embodiment, the metrology process employs a dual beam apparatus to provide increased throughput. Such dual beam apparatus are commercially available and preferably include both high energy beam and scanning electron microscopy capabilities. In this manner, the fluorine bearing gas can be locally introduced to the cross section and exposed to, for example, a focused ion beam to provide improved image contrast for scanning electron imaging.

In the case of focused ion beam exposure, the energy of the ion beam is typically between 30 keV and 50 keV, although ion beam energies less than 30 keV could be used. Ion beam energies less than 30 keV result in less sputtering than higher energy ions, thereby reducing the non-selective removal of material and increasing the contribution of the gas to the removal of surface material. Preferably, the ion beam milling process is for a period of about two minutes. Preferably, a beam current, which will vary with the size of the cross section, is from about 1 to 3,000 picoAmps, and with a beam current of about 10 to about 500 picoAmps more preferred. Skilled persons can readily adjust the etch time, gas flow, and ion beam characteristics to suit the particular materials and size of the cross section being exposed.

Optionally, the removed portion is filled with a like material similar to the removed portion. For example, if the removed portion is a dielectric material, the removed section is preferably filled with a dielectric material. The dielectric material chosen to fill the removed portion can be the same or a different dielectric material.

Referring now to FIG. 1, there is depicted an exemplary focused ion beam system generally designated reference numeral 10. The disclosure is not intended to be limited to any particular focused ion beam system in this or in the following embodiments. Focused ion beam systems particularly suitable for use are systems having gas-assisted capabilities and imaging capabilities, e.g., a scanning electron microscope.

The system 10 includes an evacuated envelope 12 having an upper portion 14 within which are located a liquid metal ion source 16 and a focusing column 18 which includes extractor electrode means and an electrostatic optical system. Ion beam 20 passes from the liquid metal source 16 through focusing column 18 and between electrostatic deflection means (i.e., deflection plates), schematically indicated at 22, toward a substrate 24, which suitably comprises a semiconductor device positioned on a stage 26 within chamber 28. An ion pump 30 is employed for evacuating the upper portion 14. The chamber 28 is evacuated, preferably with a turbomolecular and mechanical pumping system 32 under the control of vacuum controller 34. High voltage power supply 36 is connected to the liquid metal ion source 16 as well as to appropriate electrodes in the ion beam focusing column 18 for forming an ion beam 20 and directing the same downwardly. Deflection controller and amplifier 38, operated in accordance with a prescribed pattern, such as a raster pattern, provided by pattern generator 40, is coupled to deflection plates 22, whereby ion beam 20 may be controlled to trace out a corresponding pattern on the upper surface of substrate 24.

The metal source 16 typically provides a metal ion beam of gallium (although other metallic ions can be used, for example indium or aluminum). The source is capable of being focused into a sub-0.1 micron width beam at substrate 24. An electron multiplier 42 used for detecting secondary emission for imaging is connected to a video circuit and amplifier 44, the latter supplying the drive for video monitor 46 also receiving deflection signals from deflection controller and amplifier 38. The evacuated envelope 12 preferably includes a scanning electron microscope (SEM) 46 that can be used to view the results of operations performed by the focused ion beam, or more preferably, that can perform electron beam processing. SEM 46 includes an electron beam generator and an associated power supply and controls 50.

A gas source 52 is located inwardly of the side of chamber 28 by a translation device 54 adapted for positioning the source 52 via support means within bellows 56. Bellows 56 accommodates movement of the nozzle assembly and reservoir relative to the substrate 24 without affecting the vacuum within chamber 28. Gas source 52 includes a reservoir 58 and a heater 60, which may comprise a membrane type heater and which may be used for raising the temperature of a compound within reservoir 58 to a temperature for providing a suitable vapor pressure in accordance with art recognized practices. A transfer tube or nozzle 62 comprising a capillary tube such as a hypodermic needle extends from reservoir 58 and is connected thereto via control valve 64 adapted for releasing gaseous vapor. The nozzle is extended and translated in orthogonal directions substantially perpendicular to its axis employing translation apparatus 54, so that gaseous vapor can be aimed directly toward a region on the top surface of substrate 24.

A door 66 is opened for inserting the substrate 24 onto stage 26 which may be heated, and also for servicing the reservoir 58. The door is preferably interlocked so that it cannot be opened if the temperature in reservoir 58 is substantially above room temperature. A gate valve, schematically illustrated at 68, is closed before door 66 can be opened to seal off the ion source and focusing column apparatus. Bellows 56 accommodates movement of the nozzle assembly 52 and reservoir relative to the substrate without affecting the vacuum within chamber 26.

The vacuum control system along with the heater of gaseous vapor source 60 are operated to provide an appropriate vapor pressure condition for establishing a gaseous vapor flux in chamber that is directed toward substrate 24 for selective etching. To establish a given gaseous flux, the reservoir 58 is heated to a predetermined temperature as is known by those skilled in the art.

The high voltage power supply 36 provides an appropriate acceleration voltage to electrodes in ion beam focusing column 18 for energizing and focusing ion beam 20. When the ion beam 20 strikes the substrate 24 having condensed gaseous vapor adhered thereupon, the ion beam 20 provides energy for initiating a reaction between the etch-enhancing gaseous compound and the substrate as well as for sputter etching selected areas of the substrate. Deflection controller and amplifier 38 cause the ion beam 20 to be deflected in a desired pattern wherein deflection of the ion beam 20 is at a rate slow enough for etching substrate 24. Considerations regarding deflection speed, loop time, etc. are well within the skill of those in the art.

The following examples are presented for illustrative purposes only, and are not intended to limit the scope of the disclosure.

COMPARATIVE EXAMPLE 1

In this comparative example, an image of a buried feature exposed and processed in accordance with a prior art process was taken. The process exposed a gate structure, i.e., buried feature, after exposure to a focused ion beam. The focused ion beam milling process employed a beam current of 100 picoamps. During focused ion beam exposure, a selected portion of the substrate was exposed to $XeF_2$ gas for 1 second and a second exposure of 10 seconds employing a proprietary gas mixture developed by FEI Company. A scanning electron micrograph was then taken and is presented as FIG. 1. Information available the image shows a poly gate, an oxide disposed about the polygate, and metal interconnect. As shown, micrograph fails to provide any contrast or discrimination of two nitride layers disposed about the oxide and polygate structure.

EXAMPLE 2

Figure 2:
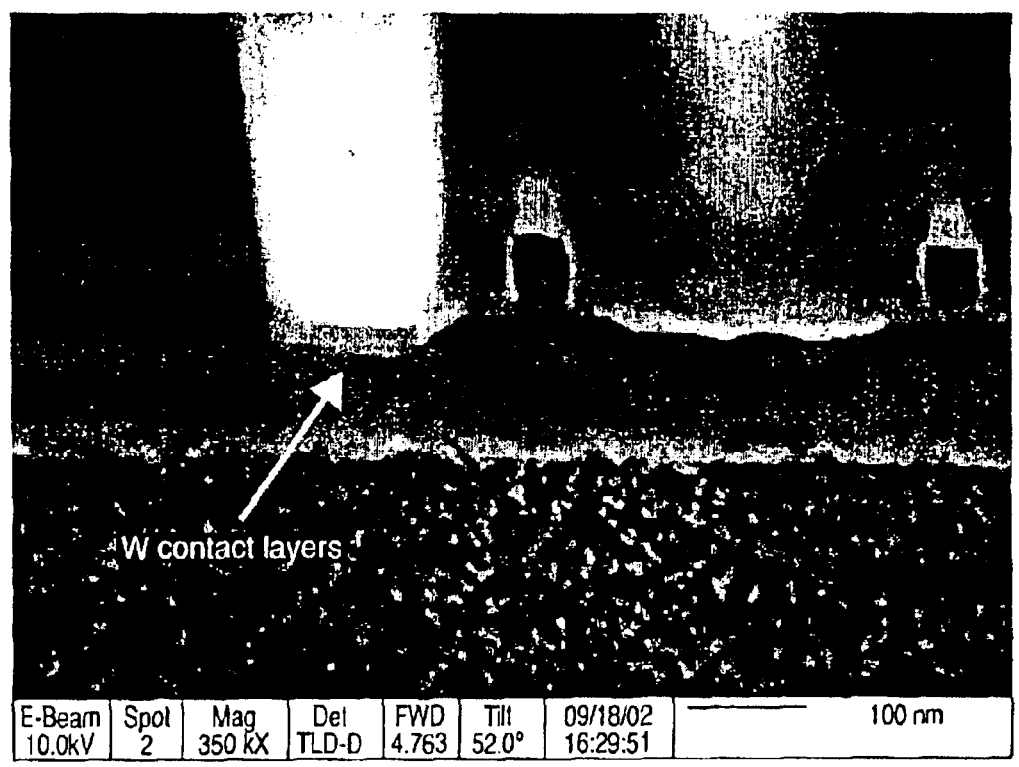
FIG. 2 is a scanning electron micrograph of an embedded gate structure employing a prior art metrology process.
Figure 3:
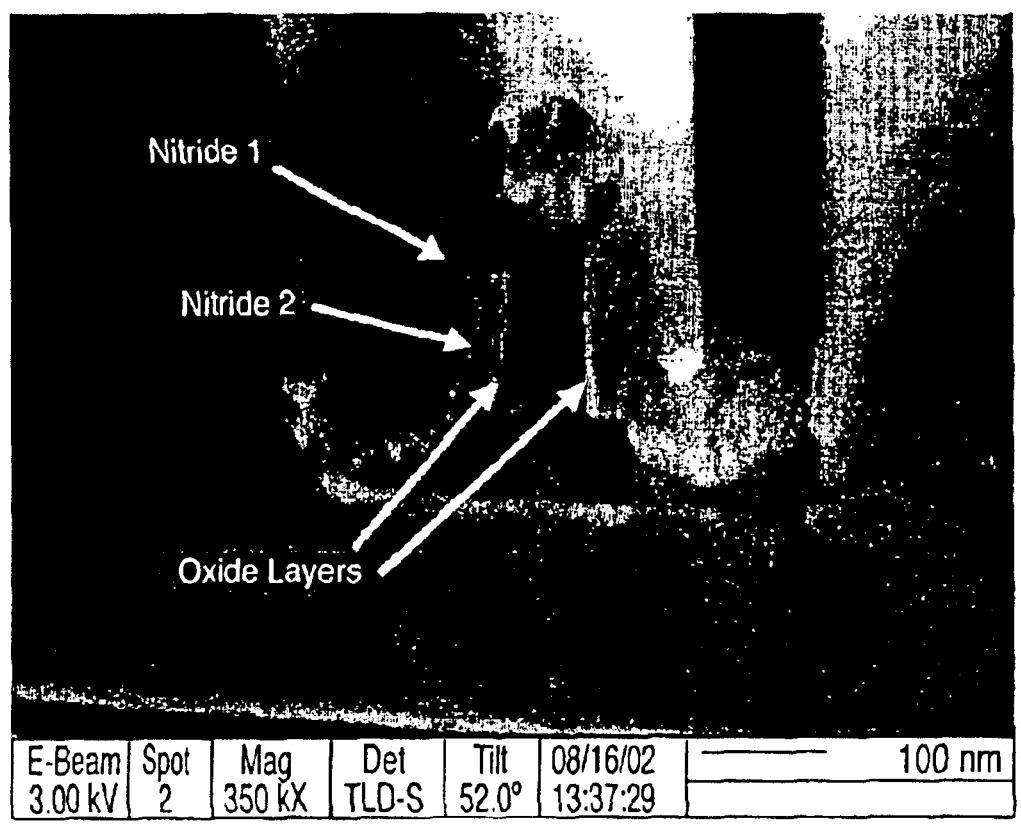
FIG. 3 is a scanning electron micrograph of an embedded gate structure employing a metrology process in accordance with the present disclosure.

In this example, an image of a buried feature processed in accordance with the present disclosure was taken. A substrate containing a buried polygate structure as in Comparative Example 1 was placed in a chamber of a dual beam FIB instrument commercially available from FEI Company. The focused ion beam milling process employed a beam current of 100 picoAmps. Subsequently, a plasma beam formed from a $CF_4/O_2$ gas mixture at a volume gas ratio of 90:10 for 10 seconds was directed at the exposed cross section. A scanning electron micrograph was then taken at an angle and is presented as FIG. 3. Information available from the image clearly shows the poly gate, the oxide layer disposed about the polygate, and metal interconnect as in FIG. 2. However, the image also provides contrast and discrimination of two nitride layers deposited about the gate oxide as labeled.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A metrology process for increasing image contrast of a buried feature, comprising:

milling a selected surface of a substrate to expose a cross section of the buried feature;

exposing the exposed cross section with a gas mixture, wherein the gas mixture comprises a fluorine bearing compound; and irradiating the exposed cross section with a high energy beam to increase image contrast of the buried feature.

2. The metrology process of claim 1, wherein the high energy beam comprises an ion beam, and electron beam, a plasma, or a laser.

3. The metrology process of claim 1, wherein milling forms a wall substantially perpendicular to a major plane of the substrate.

4. The metrology process of claim 1, further comprising recording an image of the exposed cross section at an angle from the substantially perpendicular wall.

5. The metrology process of claim 4, wherein recording the image comprises scanning electron microscopy.

6. The metrology process of claim 1, wherein the milling comprises exposing the selected surface to a focused ion beam.

7. The metrology process of claim 1, the milling comprises exposing the selected surface to a focused ion beam and a noble gas halide selected from the group consisting of $XeF_2$, $XeF_4$, $XeF_6$, $KrF_2$, $KrF_4$, and $KrF_6$.

8. The metrology process of claim 4, further comprising filling the exposed cross section subsequent to recording the image.

9. The metrology process of claim 1, wherein milling and exposing the exposed cross section occurs in a dual beam exposure apparatus.

10. The metrology process of claim 1, wherein the fluorine bearing compound comprises a formula of $C_xH_yF_z$, wherein x ranges from 1 to 4, y ranges from 0 to 9 and z ranges from 1 to 10.

11. The metrology process of claim 1, wherein the fluorine bearing compound comprises $CF_4$, HF, $NF_3$, $F_2$, $SF_6$ or a combination comprising at least one of the foregoing fluorine bearing compounds.

12. The metrology process of claim 1, wherein the fluorine bearing compound is less than about 80 parts by volume of the second gas mixture.

13. The metrology process of claim 1, wherein the gas mixture comprises the fluorine bearing compound and an oxidizing gas.

14. The metrology process of claim 13, wherein the oxidizing gas comprises $O_2$, NO, water vapor, or mixtures comprising at least one of the foregoing oxidizing gases.

15. A metrology process for enhancing an image contrast between an oxide layer in contact with a nitride layer; comprising:

exposing a cross section comprising the oxide layer in contact with the nitride layer with a gas mixture, wherein the gas mixture comprises a fluorine bearing compound; and irradiating the exposed cross section with an ion beam or an electron beam or a plasma beam or a laser to increase the image contrast between the oxide layer and the nitride layer.

16. The metrology process of claim 15, wherein the fluorine bearing compound comprises a formula of $C_xH_yF_z$, wherein x ranges from 1 to 4, y ranges from 0 to 9 and z ranges from 1 to 10.

17. The metrology process of claim 15, wherein the fluorine bearing compound comprises $CF_4$, HF, $NF_3$, $F_2$, $SF_6$ or a combination comprising at least one of the foregoing fluorine bearing compounds.

18. The metrology process of claim 15, wherein the fluorine bearing compound is less than about 80 parts by volume of the metrology mixture.

19. The metrology process of claim 15, wherein the gas mixture further comprises an oxidizing gas.

20. The metrology process of claim 19, wherein the oxidizing gas comprises $O_2$, NO, water vapor, or mixtures comprising at least one of the foregoing oxidizing gases.

* * * * *